US006000394A

United States Patent [19]

Blaha-Schnabel et al.

[11] Patent Number: 6,000,394

[45] Date of Patent: Dec. 14, 1999

[54] GENERATION OF AN AEROSOL OF AN EXACT DOSE

[75] Inventors: Ales Blaha-Schnabel, Nuremberg; Martin Knoch, Berg; Stefan Jaser, Bobingen, all of Germany

[73] Assignee: Paul Rizau Pari-Werk GmbH, Starnberg, Germany

[21] Appl. No.: 08/917,990

[22] Filed: Aug. 25, 1997

Related U.S. Application Data

[63] Continuation of application No. 08/547,995, Oct. 25, 1995, abandoned.

[30] Foreign Application Priority Data

Oct. 26, 1994 [DE] Germany ............................ 44 38 292

[51] Int. Cl.[6] ...................................................... A61M 16/00

[52] U.S. Cl. ............................... 128/200.19; 128/200.21; 128/203.12; 128/203.16; 239/338

[58] Field of Search .......................... 128/200.19, 200.11, 128/200.14, 200.18, 200.22, 203.12, 203.14, 203.15, 200.16, 200.21, 203.16, 204.17; 239/333, 342, 405; 436/165

[56] References Cited

U.S. PATENT DOCUMENTS

| | | | |
|---|---|---|---|
| 3,565,072 | 2/1971 | Gauthier | 128/200.16 |
| 3,647,143 | 3/1972 | Gauthier et al. | 128/200.14 |
| 4,018,387 | 4/1977 | Erb et al. | 239/338 |
| 4,368,850 | 1/1983 | Szekely | 128/200.22 |
| 4,611,590 | 9/1986 | Ryschka et al. | 128/203.14 |
| 4,649,911 | 3/1987 | Knight et al. | 128/200.21 |
| 4,740,475 | 4/1988 | Paul | 436/165 |
| 5,056,511 | 10/1991 | Ronge | 128/200.14 |
| 5,172,686 | 12/1992 | Anthony | 128/203.16 |
| 5,248,448 | 9/1993 | Waldron et al. | 239/338 |
| 5,297,542 | 3/1994 | Bacon | 128/200.14 |
| 5,394,868 | 3/1995 | Ambrosio et al. | 128/203.15 |
| 5,487,378 | 1/1996 | Robertson et al. | 128/200.14 |

FOREIGN PATENT DOCUMENTS

| | | | |
|---|---|---|---|
| 0 539 674 A1 | 5/1993 | European Pat. Off. . | |
| 32 38 149 A1 | 4/1984 | Germany . | |
| 40 09 067 A1 | 12/1991 | Germany . | |
| 1453605 | 10/1976 | United Kingdom . | |
| 2 272 389 | 5/1994 | United Kingdom . | |
| 2272389 | 5/1994 | United Kingdom | 239/102.2 |
| 9100117 | 1/1991 | WIPO | 128/203.15 |
| WO 91/00117 | 1/1991 | WIPO | 128/203.15 |
| 9427664 | 12/1994 | WIPO | 128/203.12 |
| WO 94/27664 | 12/1994 | WIPO . | |

*Primary Examiner*—John G. Weiss
*Assistant Examiner*—V. Srivastava
*Attorney, Agent, or Firm*—Merchant & Gould P.C.

[57] ABSTRACT

The invention relates to an apparatus for the generation of an exact dose of and making available of an aerosol and which includes: a dispersing nozzle (3) for mixing a liquid containing the effective substance with a gaseous dispersion medium while forming an aerosol, an aerosol drying vessel (4) for buffering and drying the aerosol produced by the dispersion nozzle (3), the aerosol drying vessel (4) being connected to the dispersing nozzle (3) and the aerosol being sprayed from the dispersing nozzle (3) into the aerosol drying vessel 4), a liquid supply apparatus (1) for making available and supplying defined amounts of the liquid containing the effective substance to the dispersing nozzle (3), a dispersion medium supply apparatus (2) for making available and supplying the dispersion medium to the dispersing nozzle (3) at a specified pressure, and a control means (5) connected to the supply apparatus (1, 2) for coordinating and controlling the supply of dispersion medium and the liquid containing the effectivee substance.

11 Claims, 5 Drawing Sheets

GENERATION OF AN AEROSOL OF AN EXACT DOSE

Figure 1:
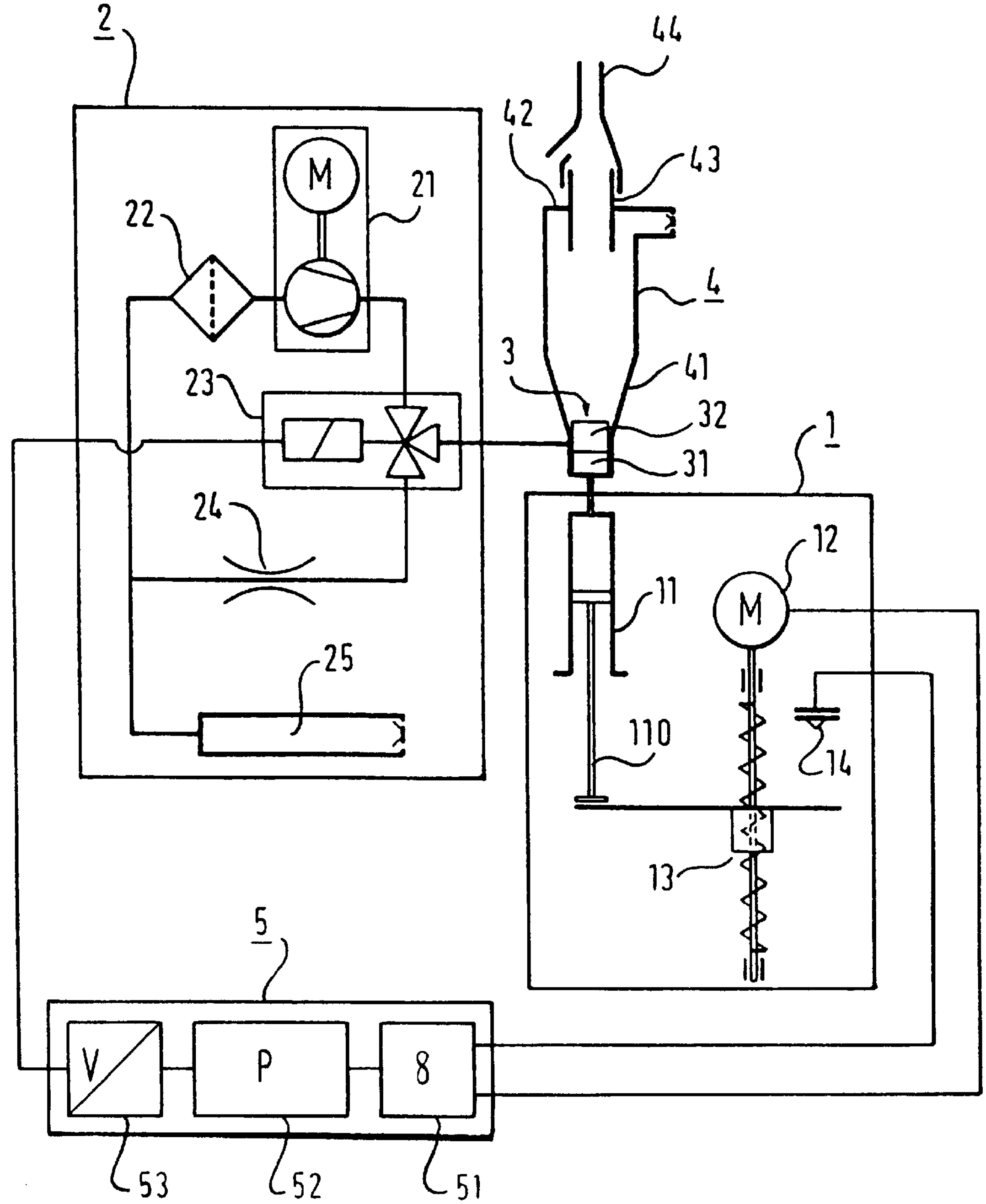

This is a Continuation of application Ser. No. 08/547,995, filed Oct. 25, 1995, now abandoned.

The invention relates to an apparatus for generating an aerosol of an exact dose for inhalation therapy.

It is necessary for carrying out an inhalation therapy in the medical field to prepare a medicament in the form of an aerosol which can be deposited in the lung. This can occur in that the medicament is initially dissolved or suspended in a liquid either alone or with saline solution as a subsequent medicament carrier. This solution or suspension is then atomised with a gaseous medium, generally air, by a dispersing nozzle and an aerosol is thus produced. The aerosol is sprayed into a buffering or drying device, the dimensions of which are adapted to the operation parameters of the dispersing nozzle. The mass flow ratio between the liquid and the dispersing air, the air humidity as well as the concentration of the medicament and the salt in the liquid can be adapted to one another in such a manner that the aerosol particles can dry to a specified size. The size of the aerosol particles determine where they are principally separated out within the body upon inhalation. As a rule, larger aerosol particles are separated out in the throat cavity while smaller particles are separated out in the bronchia or deep in the lung. It is equally important that the aerosol particles are not too small because they will otherwise be exhaled again without having been separated out.

Common pressurized air operated nozzles, known for example from DE 32 38 149 A1, operate according to the Venturi principle, i.e. a pressurized air flow is passed by an opening which is connected to a liquid reservoir, the suction created by the air flow sucking up the liquid and distributing this in the air flow. The liquid is drawn out of medicament beaker by capillaries, it being necessary to maintain the suction effect to keep the capillaries filled, i.e. a basic level of liquid must also be present. If one falls below this basic level, the atomisation becomes uncontrolled and irregular and the atomiser no longer works at the operating level. Therefore, in such an arrangement, an amount of liquid remains in the medicament beaker and adhered to the vessel walls which is not to be ignored and can not be atomised.

Usually, the medicament concentration in the liquid to be atomised is selected to be low so as not to exceed the permitted dose and to avoid encrustation and adherence to the capillary openings. However, this limits the options for dosing and leads to long atomisation times.

A further difficulty with exact dosing in common atomisers is that such apparatus are generally equipped internally with baffle plate systems, which serve as drop separators. These separators prevent drops which are too large from being inhaled. So as not to lose the medicament in the separated droplets, the separated solution is returned to the medicament beaker and collected. During the recirculation, the medicament concentration in the medication beaker increases on account of evaporation of the solvent. Such uncontrolled changes in the solution properties make a medicament output of an exact dose practically impossible. In order to reduce the influence of this effect and to keep the remaining residue amount in relation to the issued amounts small, solutions with a low medicament concentration are used, but this has the disadvantage that the treatment times are long on account of the necessarily large filling volumes (2 to 3 ml).

A method is described in U.S. Pat. No. 5,320,094 and in EP 0 574 038 A2 in which a common atomiser type is supplemented by an aerosol chamber as a store and discontinuously operated.

However, the decisive disadvantage of this method continues to be the inadequate exactness of dosing caused by the starting up and running down processes when turning on and turning off the dispersing air for the atomiser, in which the aerosol production is undefined. The further disadvantage is the medicament output itself specific to the device which amounts to 20%. The causes for this lie on the one hand in the already described structure of a common pressurized air operated atomiser and, on the other hand, in the unfavourable flow guidance through the aerosol chamber which, on account of its simple structure, has dead flow spaces and permits considerable outward leakage when being filled with aerosol.

An improvement in the dosing exactness and a considerable increase in the medicament usage specific to the device is achieved by the invention described in the following.

The invention is based on the object of providing an apparatus which permits a generation and output of an aerosol with an exact dose. The object therefore resides in permitting a dosimetric aerosol generation.

This object is solved by an apparatus by means of which a forced, controllable and exact mixing of a medicament solution with dispersion medium is realized, and which includes:

- a dispersing nozzle for mixing a liquid containing the effective substance with a gaseous dispersion medium while forming an aerosol,
- an aerosol drying vessel for buffering and drying the aerosol produced by the dispersing nozzle, the aerosol drying vessel being connected to the dispersing nozzle and the aerosol being sprayed from the dispersing nozzle into the aerosol drying vessel,
- a liquid supply apparatus for making available and supplying defined amounts of the liquid containing the effective substance to the dispersing nozzle,
- a dispersion medium supply apparatus for making available and supplying the dispersion medium to the dispersing nozzle at a certain pressure, and
- a control means connected to the supply apparatus for coordinating and controlling the supply of the dispersion medium and the liquid containing the effective substance.

Further advantageous embodiments are defined in the dependent claims.

The invention and a specific exemplary embodiment are described in the followed with reference to the drawings.

FIG. 1 schematically shows the structure of a preferred exemplary embodiment of the invention.

Figure 2A:
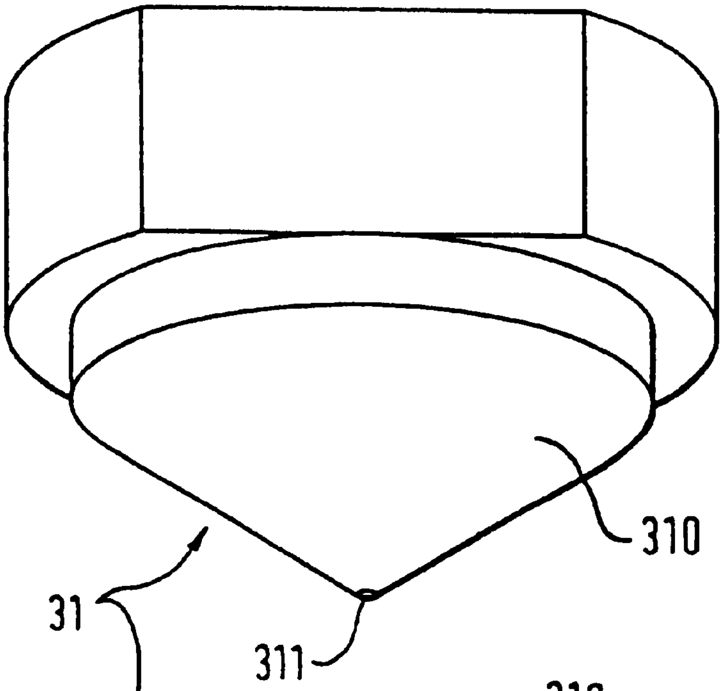
Figure 2B:
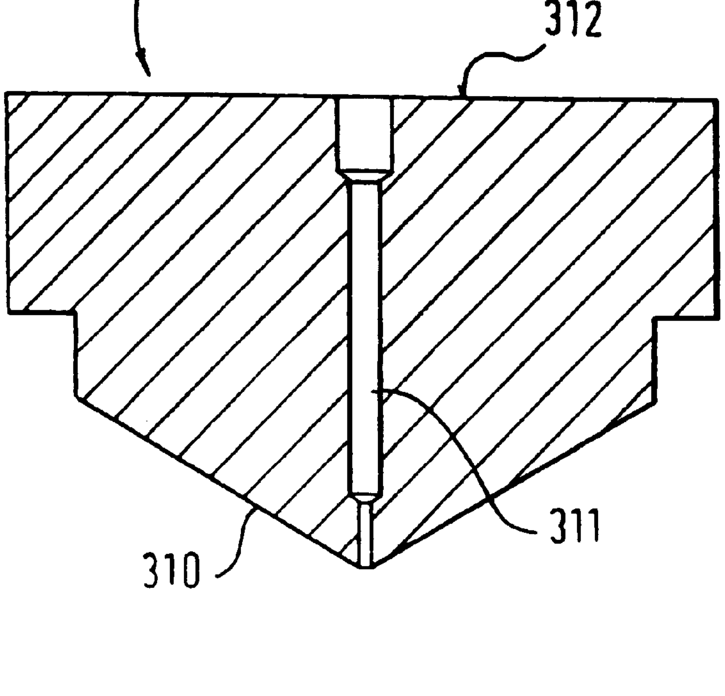

FIG. 2A–B shows a nozzle insert belonging to a preferred dispersing nozzle.

Figure 3A:
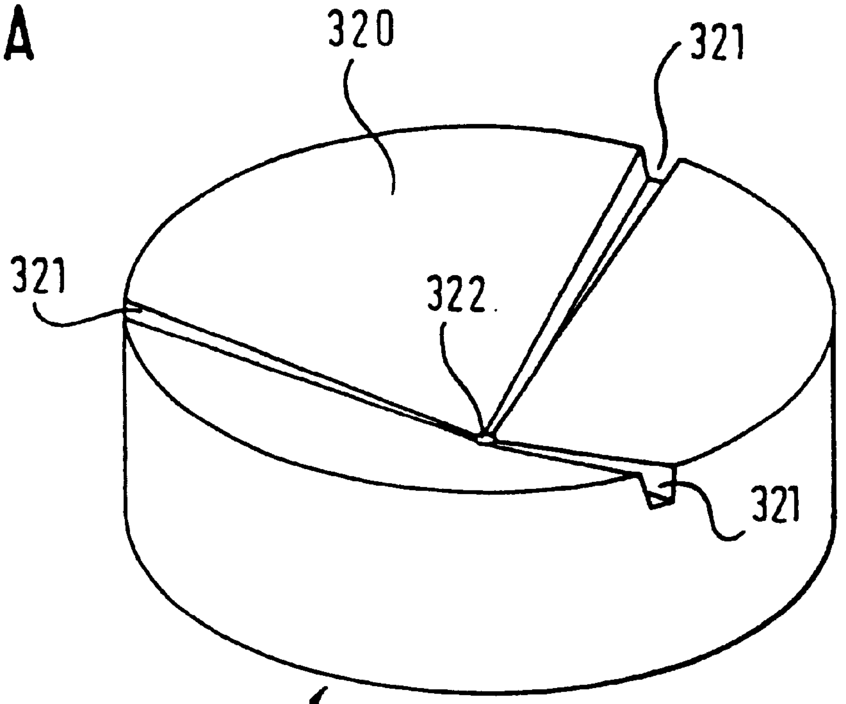
Figure 3B:
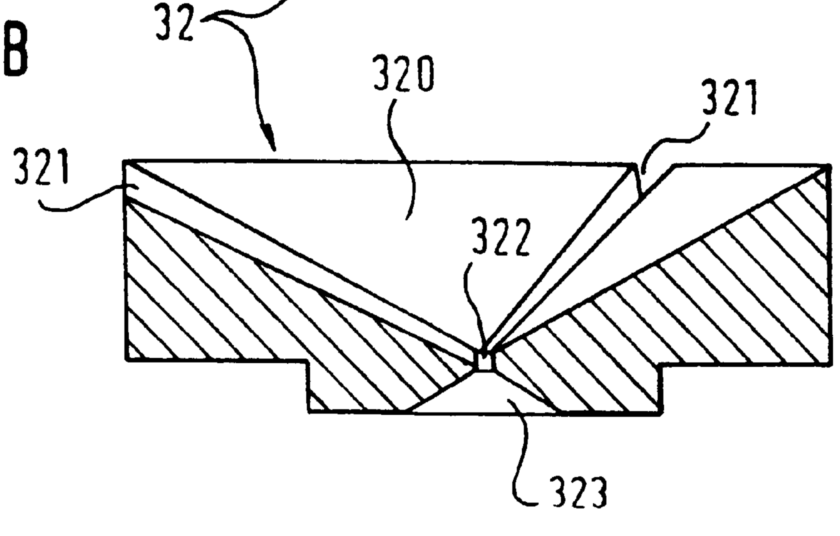

FIG. 3A–B shows a nozzle seat belonging to the preferred dispersing nozzle.

FIG. 4A–D shows the time-dependent variation of the condition of specific components of an inventive system and the time-dependent variation of control signals, respectively.

Figure 5:
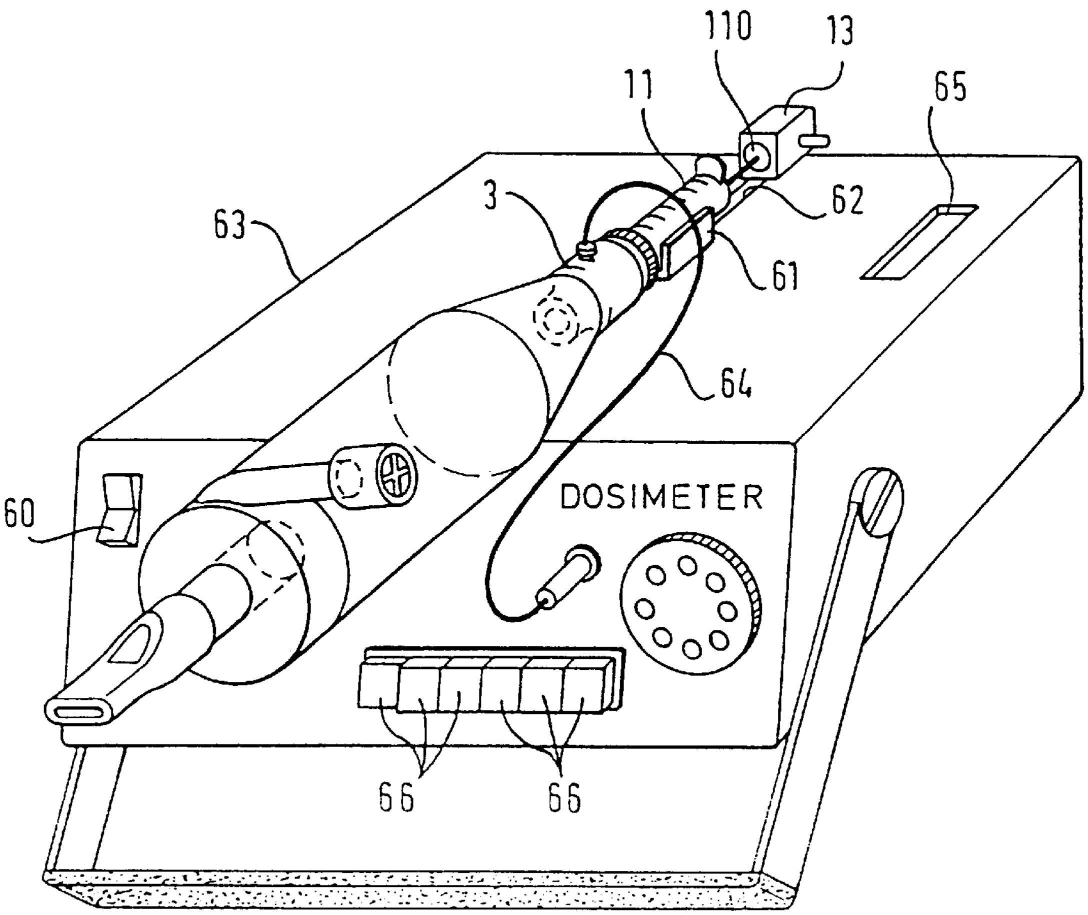

FIG. 5 shows a perspective view of a preferred exemplary embodiment.

FIG. 1 schematically shows the structure of preferred exemplary embodiment of the invention. The reference numeral 1 notes a liquid supply apparatus for making available a liquid containing the effective substance; 2 denotes a pressurized air supply apparatus for making available pressurized air as a dispersion medium; 3 denotes a dispersing nozzle by means of which the liquid and the pressurized air are mixed while forming an aerosol and sprayed into an aerosol drying vessel 4. A control means 5 connected to the supply apparatus 1 and 2 controls all operating sequences in the apparatus according to a specified program.

The supply apparatus 1 includes an injector 11 and a stepping motor 12 a linear feed 13 as well as an end switch 14. The injector is preferably a so-called GC-injector in which a thin wire-shaped piston is moved in a bore in a cylindrical glass body. The injector is securely fixed and the linear feed 13 is connected to the injector piston 110 such that an actuation of the stepping motor results in a corresponding movement of the injector piston. If the injector piston arrives at an end position, for example, when the injector is empty, the linear feed triggers the end switch 14, after which the stepping motor 12 is turned off. The injector body is fixed by a holder (not shown) and the channel is sealingly introduced into an opening provided for this in the dispersing nozzle 3.

The pressurized air supply apparatus 2 includes a compressor 21 with an upstream filter 22 and a controllable valve 23, for example a magnetic valve. This valve 23 connects the compressor outlet to the dispersing nozzle 3 or to a bypass throttle 24. Additionally, a drying member 25 is provided, which removes moisture from the ambient air drawn in by the compressor.

The dispersing nozzle 3 has two connections by means of which, on the one hand, the liquid from the injector and, on the other hand, the pressurized air from the compressor are supplied. Pressurized air and liquid are mixed to an aerosol in the nozzle and sprayed into the aerosol drying or aerosol buffering vessel.

As shown in FIGS. 2 and 3, the dispersing nozzle preferably consists essentially of two parts, a nozzle insert 31 as well as a nozzle seat 32. The partial illustrations denoted with A respectively show a perspective view, and those denoted with B indicate a cross section through the respective components. The basic shape of the nozzle insert 31 includes two flat circular cylinders with different diameters and a circular cone 310, the maximum diameter of which corresponding to that of the smaller circular cylinder and it being conjoined to this. A channel 311 is provided in the middle of the nozzle insert 31 for the liquid to be atomised and passes through the entire length of the nozzle insert 31. The liquid to be dispersed is supplied through the channel 311 to the end 312 lying opposite the circular cone 310.

The basic shape of the nozzle seat 32 is formed by two flat circular cylinders arranged coaxially with respect to one another. The free end face of the larger circular cylinder has a central circular-conical recess 320, which forms a receiving surface adapted to the shape of the support surface 310 of the nozzle insert 31. Three channels 321 are formed in the receiving surface 320 of the nozzle seat 23 for the supply of the pressurized gas and extend radially towards the middle. The channels for the pressurized gas end in a cylindrical mixing chamber 322 into which the channel 311 of the nozzle insert 31 supplying the liquid also opens after assembling the dispersing nozzle 3. The assembly of the dispersing nozzle 3 is carried out by connecting the nozzle seat 32 and the nozzle insert 31 at the support surface 310 and the receiving surface 320 in a suitable holder that additionally permits the gas and liquid-tight supply of effective substance solutions and dispersion medium to the channels 311 and 321. At the side of the nozzle seat 32 opposite the nozzle insert 31, the aerosol created in the mixing chamber 322 exits through the circular-conical outlet 323 and is sprayed into the aerosol drying vessel.

The aerosol drying vessel 4 is preferably a hollow cylinder, one end 41 of which runs into a cone. The dispersing nozzle 3 is inserted into this conically extending end. In the end of the hollow cylinder opposite the conical end 42 there is a spray tube 43 by means of which the aerosol dried in the aerosol drying vessel 4 can be inhaled by means of a mouth piece 44. The conical inflow prevents the formation of dead flow spaces and an associated deposit of droplets discharged from the dispersing nozzle onto the inner wall of the aerosol drying vessel 4.

The length of the aerosol drying vessel 4 should be adapted to the operation parameters of the dispersing nozzle 3 such a manner that there is no occurrence of droplets striking against the end of the vessel including the spray tube.

The vessel volume is also adjusted to breathing parameters such as the breathing volume and the breathing frequency of a respective patient. This means that the vessel volume is selected in such a manner that a certain patient group (adults or children, for example) can completely inhale the vessel contents in an average of one to two breaths. The dispersing nozzle 3 is preferably releasably connected to the aerosol drying vessel 4 so that various drying vessels can be used according to requirements. The aerosol produced by the dispersing nozzle 3 in the aerosol drying vessel 4 can settle and the aerosol particles can dry to a desired average size, which depends on various parameters such as effective substance concentrations of the solution and chemical properties of the solution, but also on the amount, pressure and moisture content of the dispersion medium.

The control means 5 includes a stepping motor control 51, which is connected to the stepping motor 12 and the end switch 14, and a processor 52 that controls the stepping motor control and the valve 23 via the amplifier 53.

Figure 4A:
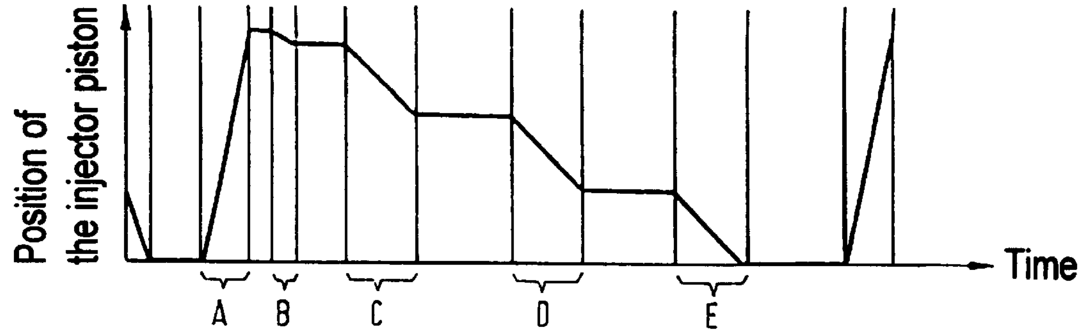
Figure 4B:
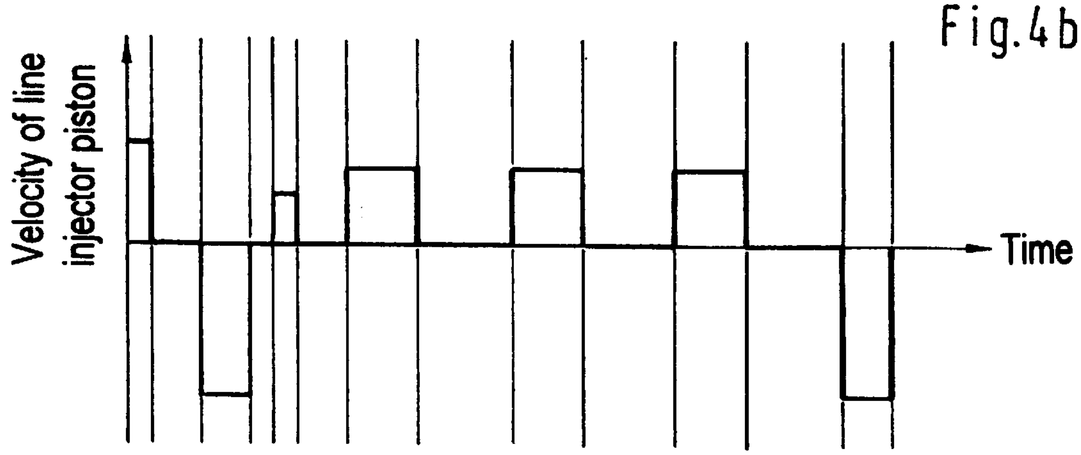

In the following, the mode of operation of the apparatus is explained with reference to FIG. 4. After turning on the apparatus, the processor 52, which runs a suitable program, activates the stepping motor control 51 that the zero point of the linear unit 13 is automatically contacted for absolute positioning. Upon the pressing of a button by a user, for example, the linear unit then moves away from the end switch so that the complete injector can be inserted and the aerosol buffering vessel can be connected. This is schematically illustrated in FIGS. 4*a* and 4*b* as step A. Following this, the patient, doctor or other person concerned is requested by a display means (not shown) to input data into the processor by means of an input unit (not shown), such as the injector size or the type of aerosol drying vessel used from which the optimum operation can then be determined for the patient.

An injector 11 filled with the liquid containing the effective substance is connected to the nozzle 3 and fixed. The feed unit 13 then moves into the starting position, as shown in the time interval B in FIGS. 4*a* and 4*b*. The piston end 110 of the injector is connected to the linear feed 13. The injector provides the advantage that it simultaneously offers a dosing possibility as well as also representing a reservoir.

Figure 4C:
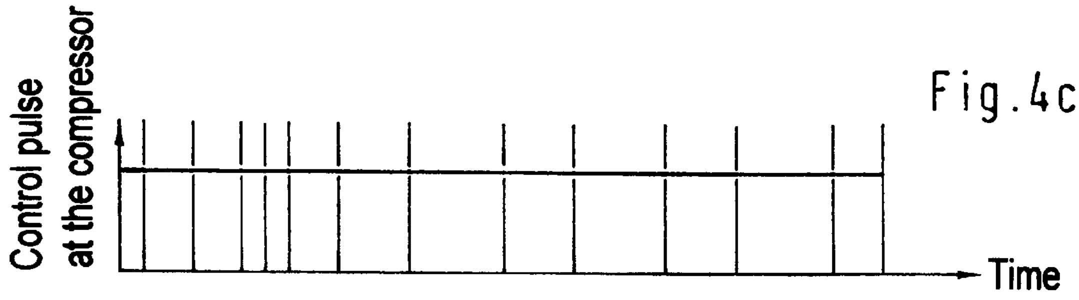
Figure 4D:
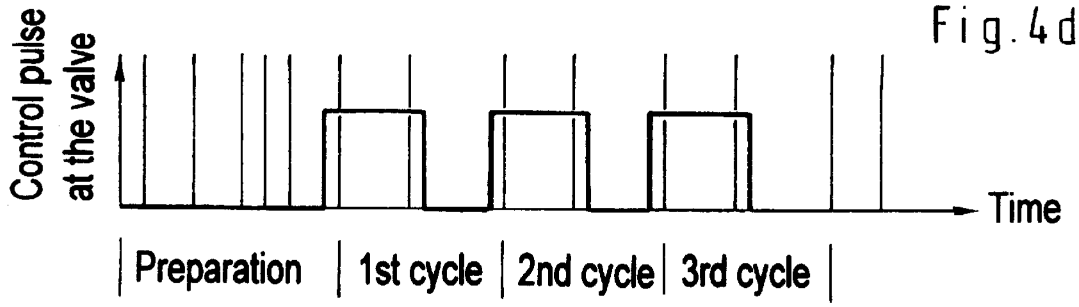

As shown in FIG. 4*c*, the compressor is in continual operation. This has the purpose of ensuring constant pressure conditions at the nozzle during use. The making available of the pressurized air for dispersion occurs by means of switching the valve 23, as shown in FIG. 4*d*. So as not to unnecessarily burden the drying member 25 with moisture, the valve 23 is switched in such a manner that, when there is no connection between the compressor and the dispersing nozzle 3, the pressurized air is supplied via a bypass throttle 24 to the compressor suction side, which releases the pressurized air again to the suction pressure. In this latter case, the supply means 2 is in short-circuit operation.

The resistance of the throttle 24 is adapted to the resistance of the nozzle so that the compressor always operates at the same operating level and immediately applies the full operational pressure upon switching to the nozzle.

In the actual atomising operation, the linear unit 13 is moved with constant velocity for predetermined time intervals so that the volume of the injector 11 is correspondingly reduced and, thus, defined amounts of the solution containing the effective substance are supplied to the dispersing nozzle 3. This is indicated by the sequential time periods C, D and E in FIGS. 4*a* and 4*b*. As illustrated in FIG. 4*d*, the valve 23 is switched in such a manner that the pressurized air supply to the dispersing nozzle 3 takes place several 100 ms before supply of the liquid solution and that pressurized air is also continuously made available several 100 ms after completion of the supply of liquid solution. The initial operation serves to bridge the starting up time of the operation level of the nozzle 3 which is produced by the volume of the pressurized air line to the nozzle 3, i.e. the compressor pressure must first by built up in this volume after each switching of the valve before this pressure is applied at the pressurized air inlet of the dispersing nozzle 3. On the other hand, the subsequent operating time of the pressurized air supply is selected in such a manner that the liquid possibly still present in the mixing space of the nozzle 3 can also be atomised.

An atomising step is preferably initiated by the patient who actuates a switch (not shown) for this purpose which is connected with the control means 5 and starts the beginning of a procedure C, D or E in FIG. 4*a*. After conclusion of the atomising procedure and after the aerosol has dried in the aerosol drying vessel to the predetermined particle size, an indication is given to the patient by means of a sound or light signal that the aerosol can be inhaled.

However, it is also possible that the atomising procedure is initiated only by the control means 5, the beginning of such an atomising procedure than preferably being indicated to the patient by means of a suitable signal.

The stepping motor control 51 and the processor 52 are preferably realized in an integrated form on a plate, the processor 52 running a suitable program for the control procedure. However, it also is possible to connect the stepping motor control with an external data processing unit, for example a PC, and to allow the entire process to be controlled by software loaded into the data processing unit. Finally, it is also possible to connect a control integrated with processor in a closed device by means of an interface with a further, external computer.

FIG. 5 shows a perspective view of such an integrated complete device as a preferred exemplary embodiment. The device is activated by means of a master switch 60. The injector is fixed in a holder 61, the channel being led into a dispersing nozzle 3 and the injector piston 110 being moved by the linear drive 13 which runs in a slot-shaped housing opening 62. The linear drive 13 is connected with the stepping motor located in the device housing 63.

The pressurized air supply to the dispersing nozzle 3 ensues by means of a line 64 which is connected with the compressor or valve located in the housing 63. The drying member 25 can be observed through a viewing window 65 by means of which the time for the required regeneration or exchange of the drying stretch can be observed. It is also possible to determine the humidity of the dispersion air electronically and to automatically switch off the device when a limiting value has been exceeded. Additionally, the device keys 66 which allow the initiation of an atomising process are provided for the input of important process data (for example, injector size, type of aerosol drying vessel and the like).

However, even further advantageous embodiments are possible. Thus, in order to control the dosing even better, a volume flow meter (not shown) can be provided that measures the breath flow of the inhaling patient. Such a volume low meter could be mounted on the aerosol drying device and, for example, be a common through-flow counter that measures the external air sucked into the aerosol drying vessel. Preferably, the determined breath flow value is supplied to the control means 5 for further processing and displayed.

A further embodiment of the dosing apparatus results from the additional use of a device for measuring the particle concentration (not shown). In this manner, the discharging efficiency of the aerosol drying vessel can be tested. Such a device could preferably determine the particle concentration between the spray tube 43 and the mouth piece 42 and, for example, consist of a laser diode (not shown) for dispersed light intensity measurement. Again, the obtained measurement value is preferably supplied to the control means 5 for further processing. However, a simple display of this value is also possible.

The effectiveness of the inventive apparatus was examined in tests. The compressor unit 2 consisted of a compressor of the Pari-Master type, which operated continuously and produced a pressure difference at the dispersing nozzle of 1.6 bar at an air throughput of 4.3 l/min. A drying stretch filled with a silicagel as an absorption means and cobalt nitrate as a colour indicator with the dimensions diameter×length=30×200 mm dried the drawn in surrounding air at 20° C. to a relative humidity of 10%. Gas-tight GC-injectors of the Hamilton company having a volume of 25–100 μl where used as injectors.

The apparatus was tested by means of two aerosol drying vessels, on the one hand with a volume of 570 ml (for adults) and, on the other hand, with a volume of 350 ml (for children). The aerosol drying vessels were respectively filled to 75% of their volume with aerosol and exhausted in two draws, a breathing cycle of 15 l/min and a breath volume of 500 ml being taken as a basis-for the large aerosol drying vessel and 20 l/min and 350 ml breath volume for the small aerosol drying vessel.

In a test with a saline solution, i.e. a 9% NaCl solution with 1% disodic chromoglycine as a tracing substance, outputs of 55% were determined. In the second test without saline solution, i.e. a 1% aqueous solution of disodic chromoglycine, an output of 65% resulted. The average aerodynamic diameter of the aerosol particles was 2.5 and 1.3 μm, respectively. A lung deposition of approximately 82% can be calculated from the measured particle distributions. Taking the outputs of the aerosol drying vessels into account, 45%–54% of the medicament used therefore could be deposited in the lung.

On account of the separate, defined and coordinated supply of dispersion medium and liquid solution to a dispersing nozzle, the present invention permits a generation and supply of a medicament aerosol of an exact dose. On the one hand, this dosimetric aerosol generation effects higher medicament output, which is particularly important in the case of expensive medication and, on the other hand, it allows a substantially improved exactness of the dose with a simultaneous shortening of the inhalation period.

We claim:

1. An apparatus for generating an exact dose of an aerosol that contains an active agent to be inhaled by a subject in need thereof, the apparatus comprising:

a dispersing nozzle for mixing a liquid containing the active agent with a gaseous dispersion medium to form an aerosol;

an aerosol drying vessel for buffering and drying an aerosol produced by the dispersing nozzle, the aerosol drying vessel being connected to the dispersing nozzle so that aerosol is sprayed out of the dispersing nozzle into the aerosol drying vessel;

a liquid supply apparatus for making available and supplying defined amounts of a liquid containing an active agent to the dispersing nozzle;

a gaseous dispersion medium supply apparatus for making available and supplying a gaseous dispersion medium to the dispersing nozzle at a specified temperature; and a control means for the liquid supply apparatus and the gaseous dispersion medium supply apparatus for coordinating and controlling the supply of gaseous dispersion medium and liquid containing active agent;

wherein the liquid supply apparatus comprises a vessel for holding liquid containing active agent, the vessel having a defined variable volume, and means for varying the volume of the vessel in a defined manner.

2. An apparatus according to claim 1, wherein the liquid supply apparatus further comprises;

an injector having a nozzle that enters the dispersing nozzle;

a stepping motor having a linear feed, the vessel comprising an injector piston connected to the linear feed; and an end switch that is actuated when the injector piston reaches a defined end position, the end switch being connected to the stepping motor, the stepping motor being be activated when the end switch is actuated.

3. An apparatus according to claim 1, wherein the gaseous dispersion medium supply apparatus further comprises a drying member for drying the gaseous dispersion medium.

4. An apparatus according to claim 3, wherein the drying member is filled with silica gel as an absorbent and cobalt nitrate as a color indicator.

5. An apparatus according to claim 1, wherein the control means include a data processor and a data input.

6. An apparatus according to claim 1, wherein the control means has an interface for connection with an external data processor.

7. An apparatus according to claim 1, further comprising means for measuring particle concentration to determine discharge of efficiency of the aerosol drying vessel.

8. An apparatus according to claim 3, wherein the drying member has an electronic humidity indicator for measuring the moisture loading state of the drying member and for automatic device turn-off when a predetermined limiting humidity value is exceeded.

9. An apparatus for generating an exact dose of an aerosol that contains an active agent to be inhaled by a subject in need thereof, the apparatus comprising:

a dispersing nozzle for mixing a liquid containing the active agent with a gaseous dispersion medium to form an aerosol;

an aerosol drying vessel for buffering and drying an aerosol produced by the dispersing nozzle, the aerosol drying vessel being connected to the dispersing nozzle so that aerosol is sprayed out of the dispersing nozzle into the aerosol drying vessel;

a liquid supply apparatus for making available and supplying defined amounts of a liquid containing an active agent to the dispersing nozzle;

a gaseous dispersion medium supply apparatus for making available and supplying a gaseous dispersion medium to the dispersing nozzle at a specified temperature; and a control means for the liquid supply apparatus and the gaseous dispersion medium supply apparatus for coordinating and controlling the supply of gaseous dispersion medium and liquid containing active agent;

wherein the dispersing nozzle comprises;

a nozzle insert through the middle of which a channel extends for supplying liquid; and a nozzle seat with channels for supplying pressurized air to a mixing chamber, the nozzle seat and the nozzle insert being connected to one another so that liquid supplied through the channel in the nozzle insert arrives in the mixing chamber that is supplied with the pressurized air.

10. An apparatus for generating an exact dose of an aerosol that contains an active agent to be inhaled by a subject in need thereof, the apparatus comprising:

a dispersing nozzle for mixing a liquid containing the active agent with a gaseous dispersion medium to form an aerosol;

an aerosol drying vessel for buffering and drying an aerosol produced by the dispersing nozzle, the aerosol drying vessel being connected to the dispersing nozzle so that aerosol is sprayed out of the dispersing nozzle into the aerosol drying vessel;

a liquid supply apparatus for making available and supplying defined amounts of a liquid containing an active agent to the dispersing nozzle;

a gaseous dispersion medium supply apparatus for making available and supplying a gaseous dispersion medium to the dispersing nozzle at a specified temperature; and a control means for the liquid supply apparatus and the gaseous dispersion medium supply apparatus for coordinating and controlling the supply of gaseous dispersion medium and liquid containing active agent;

wherein the gaseous dispersion medium supply apparatus comprises:

a gas compression apparatus; and a valve means controlled by the control means, switchable between positions for supplying gas to the dispersion nozzle and for supplying gas back to the gas compression means.

11. An apparatus for generating an exact dose of an aerosol that contains an active agent to be inhaled by a subject in need thereof, the apparatus comprising:

a dispersing nozzle for mixing a liquid containing the active agent with a gaseous dispersion medium to form an aerosol;

an aerosol drying vessel for buffering and drying an aerosol produced by the dispersing nozzle, the aerosol drying vessel being connected to the dispersing nozzle so that aerosol is sprayed out of the dispersing nozzle into the aerosol drying vessel;

a liquid supply apparatus for making available and supplying defined amounts of a liquid containing an active agent to the dispersing nozzle;

a gaseous dispersion medium supply apparatus for making available and supplying a gaseous dispersion medium to the dispersing nozzle at a specified temperature;

a control means for the liquid supply apparatus and the gaseous dispersion medium supply apparatus for coordinating and controlling the supply of gaseous dispersion medium and liquid containing active agent; and a volume flow meter mounted on the aerosol drying vessel for measuring and displaying a breath flow of a subject using the apparatus.

* * * * *